US011389672B2

(12) United States Patent
Santana Rodriguez

(10) Patent No.: US 11,389,672 B2
(45) Date of Patent: Jul. 19, 2022

(54) SYSTEM AND METHOD FOR THE ULTRASONIC TREATMENT OF FRACTURES, BONE, MUSCLE AND TENDON INJURIES, POST-SURGERY PAIN AND OSTEONECROSIS IN HUMAN AND VETERINARY MEDICINE, AND USES THEREOF

(71) Applicant: NORCRI INVEST, S.L.

(72) Inventor: Norberto Santana Rodriguez, Las Palmas de Gran Canaria (ES)

( * ) Notice: Subject to any disclaimer, the term of this patent is extended or adjusted under 35 U.S.C. 154(b) by 917 days.

(21) Appl. No.: 16/081,950

(22) PCT Filed: Mar. 1, 2017

(86) PCT No.: PCT/ES2017/000021
§ 371 (c)(1),
(2) Date: Sep. 3, 2018

(87) PCT Pub. No.: WO2017/149173
PCT Pub. Date: Sep. 8, 2017

(65) Prior Publication Data
US 2020/0289854 A1 Sep. 17, 2020

(51) Int. Cl.
A61N 7/00 (2006.01)
G16H 20/40 (2018.01)
(Continued)

(52) U.S. Cl.
CPC ............... *A61N 7/00* (2013.01); *G16H 10/60* (2018.01); *G16H 10/65* (2018.01); *G16H 15/00* (2018.01);
(Continued)

(58) Field of Classification Search
CPC .. A61N 7/00; A61N 2007/0013; G16H 10/60; G16H 20/40; G16H 40/67;
(Continued)

(56) References Cited

U.S. PATENT DOCUMENTS 7,426,475 B1 9/2008 Tangellapally et al.
2008/0155077 A1 6/2008 James
(Continued)

FOREIGN PATENT DOCUMENTS

CN 101306228 A 11/2008
CN 101362005 A 2/2009
(Continued)

OTHER PUBLICATIONS

Chinese Office Action Issued in Chinese Application No. 201780018320.1 dated Jul. 19, 2019; 5 Pages.
(Continued)

*Primary Examiner* — Hien N Nguyen
(74) *Attorney, Agent, or Firm* — Bryan D. Zerhusen, Esq.; Nicholas R. Herrel, Esq.; Cantor Colburn LLP

(57) ABSTRACT

The invention consists of an electronic system for controlled and independent treatment of fractures, bone, muscle and tendon injuries, post-surgery pain and osteonecrosis, composed by a portable ultrasound generator, electronic prescription, centralised web services platform and computer program for ultrasonic treatment both within and outside the sanitary field, in the fields of human and veterinary medicine. The method controls the treatment applied, the charge prescribed by healthcare professionals by means of an electronic prescription, which can be administered by the patients themselves or by non-healthcare professionals independently, under the control of a computer program and a web platform used to activate the therapeutic equipment, write and delete the electronic prescription, transfer data stored in the therapeutic equipment to the web services platform to analyse the quantity and quality of the treatments, and update the program. Portable generator of ultrasonic pulses with set, unalterable parameters for the treat-
(Continued)

ment of thorax, rib and sternum fractures, and of pain after thoracic surgery.

5 Claims, 2 Drawing Sheets

(51) Int. Cl.
| | |
|---|---|
| *G16H 40/67* | (2018.01) |
| *G16H 40/20* | (2018.01) |
| *G16H 15/00* | (2018.01) |
| *G16H 10/65* | (2018.01) |
| *H04L 67/02* | (2022.01) |
| *G16H 10/60* | (2018.01) |

(52) U.S. Cl.
CPC ............ *G16H 20/40* (2018.01); *G16H 40/20* (2018.01); *G16H 40/67* (2018.01); *H04L 67/02* (2013.01); *A61N 2007/0013* (2013.01)

(58) Field of Classification Search
CPC ........ G16H 40/20; G16H 15/00; G16H 10/65; H04L 67/02; G06F 2221/2141; G06F 21/34; G06F 21/35; G06F 21/6218
See application file for complete search history.

(56) References Cited

U.S. PATENT DOCUMENTS

| | | |
|---|---|---|
| 2009/0254008 A1 | 10/2009 | Shields, Jr. |
| 2010/0063834 A1 | 3/2010 | Mukherjee |
| 2013/0253952 A1 | 9/2013 | Burke et al. |
| 2013/0310726 A1 | 11/2013 | Miller et al. |
| 2015/0088982 A1* | 3/2015 | Johnson ............. H04L 67/1004 709/203 |
| 2015/0213204 A1 | 7/2015 | Bose et al. |

FOREIGN PATENT DOCUMENTS

| | | |
|---|---|---|
| CN | 104380296 A | 2/2015 |
| EP | 2441409 A1 | 4/2012 |
| JP | 2006268186 A | 10/2006 |
| WO | 9847568 A1 | 10/1998 |
| WO | 2011133628 A1 | 10/2011 |
| WO | WO2011133628 A1 | 10/2011 |

OTHER PUBLICATIONS

International Search Report Issued in International Application No. PCT/ES2017/000021 dated Jul. 3, 2017; 3 Pages.
Written Opinion Issued in International Application No. PCT/ES2017/00021 dated Jul. 3, 2017; 6 Pages.

\* cited by examiner ly described.

SYSTEM AND METHOD FOR THE ULTRASONIC TREATMENT OF FRACTURES, BONE, MUSCLE AND TENDON INJURIES, POST-SURGERY PAIN AND OSTEONECROSIS IN HUMAN AND VETERINARY MEDICINE, AND USES THEREOF

Continuous or pulsed ultrasounds are used in clinical practice to treat bone fractures of the limbs, delayed consolidation, and muscle and tendon injuries.

The present invention refers to an electronic system for the controlled and autonomous treatment in general of bone fractures, bone-muscle-tendon injuries, post-surgical pain and osteonecrosis, comprising: a) a portable ultrasounds generator, b) an electronic prescription; c) a centralized web services platform; and d) a software application. This system allows patients to be treated with ultrasounds both in a hospital setting and in their home or anywhere else, through a simple, reliable, secure and manageable methodology that minimizes the likelihood of human error and provides multiple benefits to both patients and healthcare professionals in the fields of medicine and veterinary.

The system allows that control of the treatment applied to the patient is independent of the electronic equipment used, to load the treatment prescribed by healthcare professionals in an electronic prescription that enables the treatment to be administered by the patient or non-health professionals autonomously, without possibility of error, in a comfortable and safe manner, being monitored through a software application and a web platform that are used to activate the treatment equipment, write and erase electronic prescriptions, transfer the data stored in the treatment equipment to analyze the quantity and quality of treatment, and update the software of the treatment equipment.

Furthermore, more specifically, the present invention also refers to a portable generator of pulsed ultrasounds with defined, not modifiable, parameters for the treatment of thoracic, rib and sternum fractures and post-surgical thoracic pain based on the same electronic system previously described.

FIELD OF THE INVENTION

The present invention pertains to the field of physical methods for therapeutic use and it is based on an electronic system and method for the application of ultrasounds to enhance ambulatory therapy through a portable, simple, reliable, safe and inexpensive device controllable through a software application and a web platform to be used in the fields of veterinary and medicine for the treatment of bone fractures, bone-muscle-tendon injuries, post-surgical pain and osteonectrosis.

BACKGROUND

Ultrasounds are used to treat limb fractures and complications derived from delayed union of those (pseudoarthrosis); as well as for muscle-tendon pathologies. Ultrasound treatments are usually carried out in health centers, requiring the patient to repeatedly visit the health center which difficult treatment compliance. They also normally require a healthcare professional to program each session and administer the treatment.

U.S. Pat. No. 4,530,360 by Duarte discloses a non-invasive therapeutic methodology and an equipment for applying ultrasound pulses to the skin in an area near to the bone injury, being necessary that a healthcare professional adjusts frequency, duty cycle, and potency, and chooses the size of the applicator and its position on the patient's skin. Besides this, to apply the treatment, it is necessary for an operator to hold the applicator in the chosen application site for the duration of the treatment, immobilizing both the patient and the operator.

U.S. Pat. Nos. 5,003,965, 5,186,162 and 5,211,160 by Talish and Lifshey describe an ultrasound system where the transducer along with a small battery and a RF generator are located in a small applicator module which is attachable to the patient's body. Additionally, it increases patient safety in case of short circuits in the applicator module's connector, making an optic, not an electric, coupling of signals between the central unit and the applicator module. The goal was to create an ergonomic, portable, ultrasound system of therapy that allows patient mobility while receiving treatment.

Furthermore, Talish et al point out in the U.S. Pat. No. 6,261,249, that ultrasound equipments adapted for domiciliary use respond to a configuration that could be arbitrarily set by anyone with access to the equipment, so that treatments could not be controlled neither monitorized by healthcare professionals. In that patent, Talish et al. highlight a number of features that the equipment should control such as: flexibility in the start time for the daily sessions always that a maximum of 2 sessions are given for each period of 36 hours; the possibility of temporarily arresting treatment; detect and inform the user of the absence of gel between the transducer and skin; the ability to measure and correct the potency level delivered to the patient; and creating a historical record of the treatments received by the patient over a time.

The equipment proposed by Talish et al. turns off automatically once the patient has received therapy. To re-enable it, healthcare professionals must access the equipment using a secret code or a smart battery to program a new treatment on the equipment.

OBJECTS OF THE INVENTION

Establish an electronic, safe and reliable system for autonomous ultrasounds treatment through an electronic prescription, controlled by a centralized web platform and a software application that allows control of the treatment applied independently of the equipment used, providing a new approach to the field of ultrasounds treatment which is also verifiable and controllable and that minimizes the likelihood of human error.

Design a safe, universal, simple, easy to use and reliable portable ultrasounds generator, capable of supplying different parameters of dose and duration of treatment applicable to different types of pathologies such as bone fractures (in general) and their consolidation delays, muscle-tendon injuries, post-surgical pain, and osteonecrosis so that it can be used in the fields of medicine and veterinary by the own patient or non-healthcare professionals without requiring an intermediate health operator to schedule and dispense treatment.

Allow the patient to administer the treatment domiciliary without possibility of error in the prescribed doses and treatment duration and allow healthcare professionals to analyze the development of treatment and the quantity and quality of the sessions, once the treatment is completed.

Based on the previous objectives, design a pulsed ultrasound generator with specific, non-modifiable, dose and duration parameters, with which broaden the scope of therapeutic action of ultrasounds to thoracic, rib and sternal fractures for which there is currently no specific treatment, as well as to post-surgical thoracic pain, in the fields of Medicine and Veterinary.

DESCRIPTION OF THE INVENTION

The ultrasounds treatment system of the present invention comprises a centralized web services platform (WSP), a software application (APP), a set of programmable electronic prescriptions (PEP), at least one digital patient file (ET), and a portable ultrasounds treatment equipment (UTE).

The Web Services Platform (WSP) provides a set of services directed to healthcare professionals, which are always available via the Internet. Healthcare professionals may introduce electronic treatments (ET) in the WSP, share those ETs and their experiences with other professionals, assign treatments to their patients, monitor the compliance of the assigned treatments, and record the results and incidents encountered.

WSP consists of a load balancer which distributes service requests among one or more servers, and a single database. Servers communicate internally with the database using a local area network that is not accessible from outside.

The PEP or set of programmable electronic prescriptions is a physical device with enough capacity to store the ET, the PEP being a cheap, lightweight, transportable and durable digital support. As an example, but not limited, the following devices may be used: NFC cards, USB storage devices, memory cards, QR codes printed on different surfaces, among others.

The ET is a digital file that includes data about patient identity, diagnosis, all the technical parameters of the prescribed treatment, and a digital signature that ensures that the previously described data have not been manipulated by unauthorized parties.

The internal structure of the UTE is shown in the block diagram of FIG. 2 and comprises the following modules: a power supply, a battery, a system controller, a non-volatile random-access memory, a communication card, a real-time clock, the user interface, a RF oscillator, a pulse modulator, a transducer amplifier, a piezoelectric transducer which can be an internal or external part, and the monitor of therapy.

The power supply manages the energy of the UTE. Among its functions are: to charge the battery; to feed digital systems; to indicate the charge level of the battery through the Charge signal to the system controller; to indicate to the system controller whether the equipment is battery powered or not through the Battery signal; and to put the system into a low-power mode in response to the Standby command from the system controller.

In the low-power mode, the RF oscillator, the pulse modulator, the transducer amplifier, the piezoelectric transducer and the monitor of therapy do not receive energy, so that these modules are temporarily inoperative.

The system controller is a digital system based on a commercial microcontroller and it contains at least, a program memory, a data memory, digital input and output ports, analog input and output ports (through ADC and DAC converters), a set of user interruptions, and optionally, a timer subsystem. Its function is to control the distinct modules of the UTE by the sequential execution of a control program that is stored inside.

The real-time clock supplies a reference of the actual date and time to the system controller. It contains its own battery so that its operation does not depend on the main battery.

The user interface, as the module responsible of interacting with the patient, communicates with the system controller through a bus of signals for the user interface. The user interface may contain one or more of the following elements: a power button, a speaker, and a touchscreen.

The RF oscillator comprises a variable frequency synthesizer that generates a sine wave signal OSC, which frequency is the wave basis of the ultrasound, and depends on the digital code at the input Fosc. Additionally, the RF oscillator generates a square wave signal with a fixed frequency of 1 MHz. Therefore, the interval between rising edges of this signal is exactly a time of 1 µs. Both signals enter to the pulse modulator.

The method to carry out treatment according to the present invention starts form a program that can set the following modes: standby mode (READY), treatment mode (RUN), treatment-in-pause mode (PAUSE), data dump mode (DUMP) and program update mode (FLASH). At least READY, RUN and DUMP modes must be present, with FLASH and PAUSE modes being optional.

In READY mode, the UTE displays a summary of the device status to the patient through the user interface. This summary must include the following information: the date and time provided by the real time clock, the level of charge in the battery, and whether the battery is charging or not. In this mode, the system controller commands the power supply to activate the low-power mode through the standby signal. Whenever the UTE detects via the battery signal that it is plugged to the mains, the system controller must remain in READY mode.

If the communication card receives incoming data, the system controller verifies the authenticity and integrity of the data by checking its digital signature. If the signature is correct it will proceed as follows depending on the kind of incoming message: If the received message is a valid ET, the system controller checks whether the current date and time, provided by the real time clock module, are within the range established in the ET; and also whether the time elapsed between the last treatment, that is stored in the nonvolatile memory, satisfies the specification of the ET. If so, the system controller goes to RUN mode. If the received message is a memory dump command, the system controller will go to DUMP mode. If the received message is a program update request, the system controller will go to FLASH mode.

In RUN mode, the UTE displays through the user interface the remaining time of treatment and instructions for positioning and fixing to the body the piezoelectric transducer. Once the programmed treatment time has concluded, the system controller will go to READY mode. In RUN mode, the patient has the option to pause the treatment momentarily. If the patient interacts with the user interface in this way, or when an alarm is triggered, the system controller will go to PAUSE mode. In RUN mode, if the UTE detects that it is plugged to the mains (Battery), an alarm is generated, so that the system controller will go to PAUSE mode. Other alarm conditions are: battery level too low, detection of a short circuit in the piezoelectric transducer by the monitor of treatment, or detection of an open circuit in the piezoelectric transducer. In RUN mode, the power transmitted to the patient in $mW/cm^2$ in continuously calculated from the data provided by the monitor of treatment. An example of the data that the monitor of treatment must provide to the system controller are: the size of piezoelectric transducer (section in $cm^2$), the voltage (mean square value) at the piezoelectric transducer, and the current (mean square value) through the piezoelectric transducer. Once calculated and stored the level of potency transmitted to the patient, the system controller compares this value to that stored in the ET and acts on the gain factor Gain of the amplifier transducer so that the potency transmitted to the patient matches the nominal potency of the treatment.

In PAUSE mode, the remaining time of treatment is stopped, and the output potency is deactivated via the output_enable signal that goes into the transducer amplifier. The patient has the option to continue with the treatment by interacting with the user interface. If the patient requests to continue and there are not alarm conditions, then the system controller will go to RUN mode.

In DUMP mode, all information recorded in the nonvolatile random-access memory regarding treatment sessions performed by the UTE is sent through the communication card. Once the data transfer has been successfully confirmed, the system controller deletes data stored in the nonvolatile memory and goes to RUN mode. In FLASH mode, the UTE receives a sequence of bytes though the communication card. Such a sequence is checked against transfer errors. If transfer has been successfully confirmed, the system controller deletes the program memory of the microcontroller and writes the new received sequence of bytes in this area. Next, the microcontroller goes to RUN mode and the microcontroller is reseted with the new program.

The procedure for implementing the operation of the system develops as follows:

The pulse modulator receives from the system controller the activation Ton and deactivation Toff times that set the duty cycle of the pulsed ultrasound signal; and receives from the RF oscillator the sine wave signal OSC and the square signal. The pulse modulator generates a modulated signal mod_out by cyclically repeating the following sequence: connect the modulated signal mod_out to the sine wave signal OSC; count Ton cycles of the square signal REF; disconnect the output signal mod_out from the sine wave signal OSC; count Toff cycles of the square signal.

The transducer amplifier receives the modulated signal mod_out from the pulse modulator and amplifies it and converts the ultrasound energy to be effectively applied to the patient through the piezoelectric transducer. During therapy, the gain factor Gain is continuously adjusted by the system controller. This continuous adjustment is recorded in the nonvolatile random-access memory. The transducer amplifier receives the output_enable signal from the system controller that connects or disconnects the output potency. When connected, the transducer amplifier connects the output potency to the piezoelectric transducer. When disconnected, the piezoelectric transducer does not receive any potency.

The monitor of treatment collects and delivers a sufficient set of measures throughout therapy to the system controller, allowing it to adjust and calibrate the treatment and to monitor the presence of alert situations. As an example, some alert situations are: lack of gel on patient's skin, the existence of a short circuit in the connector of the piezoelectric transducer, the disconnection of the piezoelectric transducer, or lack of contact between the piezoelectric transducer and patient's skin. In any of these cases, the monitor of treatment will alert the system controller The particular implementation of the transducer amplifier and the monitor of treatment depends on the kind of piezoelectric transducer chosen, since each manufacturer works with different materials, sizes of electrodes, connectors and methods of application. The methodology of the present invention is not limited to any piezoelectric transducer in particular.

The communication card is the subsystem responsible of the digital data transfer with external devices accordingly with one or more protocols and standards such as NFC (ISO 14443), WiFi (IEEE 802.11), Ethernet (IEEE 802.3), Bluetooth (IEEE 802.15) or through an USB port, allowing the UTE to read the PEP as well as to establish a bidirectional communication with any device that runs the APP through compatible communication protocols.

The UTE must receive a valid, digitally signed ET through the communication card in order to activate. So, the ET acts as a customized digital key that the patient needs to start each treatment session. The ET can be read from a PEP or it can be received from an external device that runs the APP using any compatible communication protocol. Once the UTE has been activated, the treatment session proceeds with the highest reliability and safety guarantees for the patient. Additionally, the UTE collects and stores relevant data during the treatment sessions, these data being later transferred to the PSW through the APP.

Before beginning with the treatment, the UTE needs that a piezoelectric transducer is located and fixed on patient's skin. The UTE may include the piezoelectric transducer as an internal part or it may be externally connected with a cable and a connector. The kind of cable, connector and the method used for fixing the transducer to the patient's skin are outside the scope of this invention.

To receive each treatment session, the patient must first activate the UTE and then follow the instructions displayed on the screen. The UTE may be activated by reading a PEP or directly by the digital transfer of an ET through the APP. The patient must charge the UTE periodically to prevent it from running out of battery during the treatment session. During the treatment session, the UTE displays the remaining session time and continuously adjust potency level, oscillation frequency, and modulation parameters accordingly to the information stored in the EP. It will continuously monitor a set of securities, such as the battery level, the presence of gel between the transducer and the patient's skin, a short circuit in the connector of the transducer or a disconnection of the transducer device. Both ultrasound potency delivered to the patient and any alarm that is triggered during the treatment session are stored in the UTE.

After the treatment, all these data can be downloaded from the UTE and may be analyzed in the WSP.

Healthcare professionals have the right to use the WSP through an identity verification system. In this platform of services, healthcare professionals, among other services, may: 1) authorize third parties to make use of the APP to perform maintenance on UTEs and PEPs; 2) discharge patients and establish their diagnosis; prescribe electronic treatments (ETs) to their patients; 3) set the technical characteristics of the ETs associated with each diagnosis; 4) review the data collected in the UTE during treatment sessions; 5) evaluate the effectiveness of the prescribed treatments; 6) share ETs and their assessments with other professionals; 7) establish dialogues and consultations with other professional users of the WSP.

Maintenance operations are performed through the APP, which is available for different platforms, the APP functions being: 1) schedule a PEP with the ET prescribed to a patient so that the patient can downloaded it comfortably at home; 2) completely erase a PEP; 3) activate a UTE with an ET prescribed to a patient; 4) dump the data recorded in the UTEs during the various sessions of treatment on the WSP; and 5) update the software of the UTE. In this way, patients receive an ET and a PEP customized for their treatment.

Furthermore, those patients who have a UTE at home and have been previously diagnosed, have the option of acquiring a new PEP in a treatment center, or they can use the APP to acquire an ET suitable for their diagnosis, from anywhere, at any time and under the supervision of healthcare professionals Once treatment is completed, healthcare professionals can use the APP to dump on the WSP the information recorded in the UTEs and erase the information stored both in the UTE and the PEP so that they can be reused. Healthcare professionals can use the APP to update the software of the UTE.

From that moment, healthcare professionals can access the WSP to review and validate the compliance of treatment and assess its effectiveness.

The present invention can be applied to different uses, among which are the following:
Use of the system and method for the ultrasound treatment of bone fractures in general and their consolidation delays
Ultrasound treatment of limb fractures and their consolidation delays
Ultrasound treatment of osteo-muscular and tendon injuries
Ultrasound treatment of acute or chronic postsurgical pain
Ultrasound treatment of osteonecrosis injuries
Ultrasound treatment of thoracic, costal, sternal factors and their consolidation delays
Ultrasound treatment of costal and sternal factors and their consolidation delays and of postsurgical thoracic pain with a portable generator that emits a non-modifiable dose of pulsed ultrasound of 1 Mhz frequency, 0.5 W/cm$^2$ intensity, applied to 10% using 1 ms pulses every 9 ms (50 mw/cm$^2$) with a duration of 1 min/cm$^2$ of area to be treated.

BRIEF DESCRIPTION OF THE DRAWINGS

For a better understanding of the invention, reference is made to the following description and accompanying drawings, in which.

DESCRIPTION OF A PREFERRED EMBODIMENT

Figure 1:
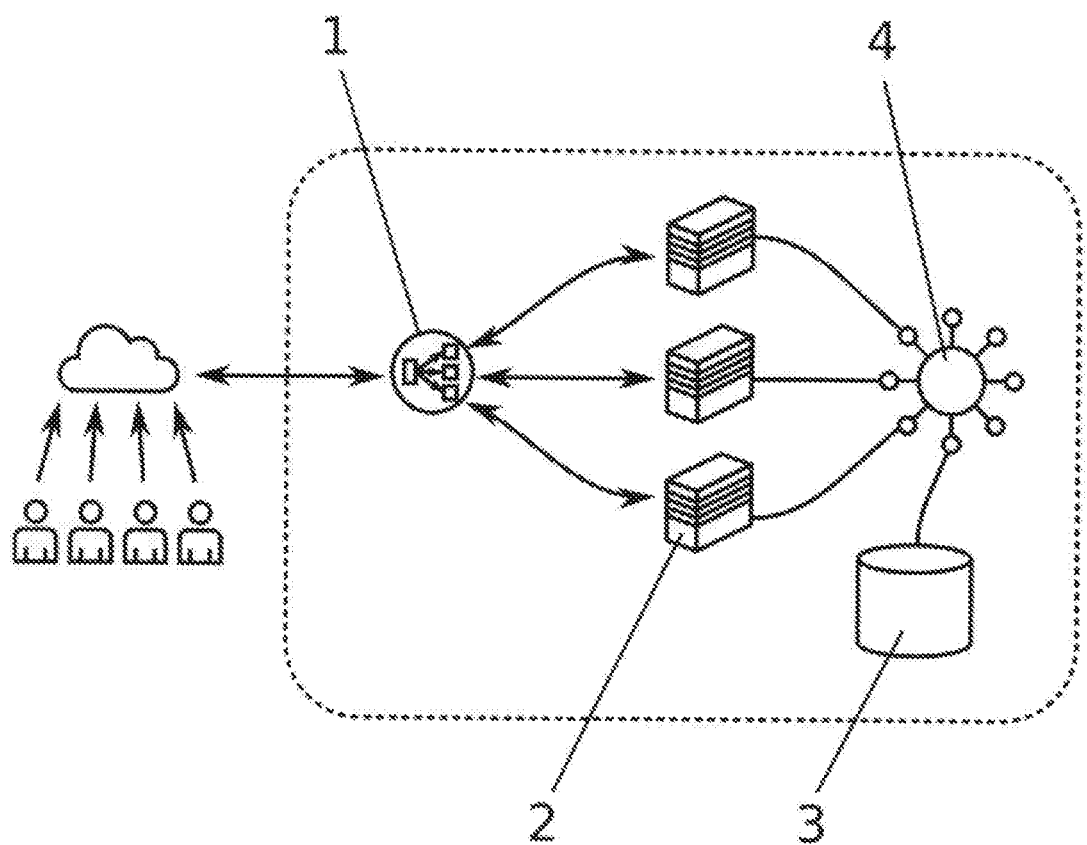
FIG. 1 shows the structure of the web services platform, WSP.
Figure 2:
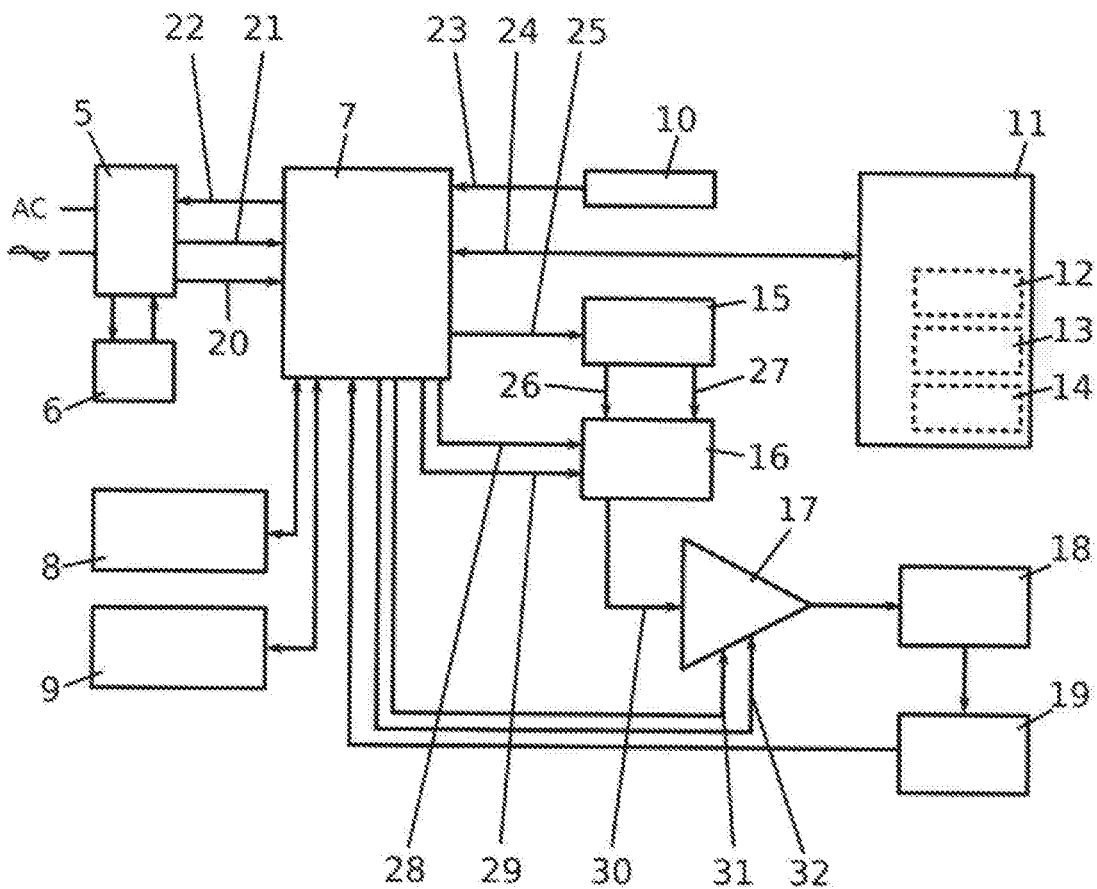
FIG. 2 shows the block diagram of the ultrasound treatment equipment, UTE.
The numerical references of the figures correspond to the following constitutive elements of the invention:
1. Load balancer
2. Servers
3. Database
4. Local Area Network
5. Power supply
6. Battery
7. System controller
8. Nonvolatile memory
9. Communications card
10. Real time clock
11. User interface
12. Power button
13. Speaker
14. Touchscreen
15. RF oscillator
16. Pulse modulator
17. Transducer amplifier
18. Piezoelectric transducer
19. Therapy monitor
20. Charge signal
21. Battery signal
22. Standby
23. Date and time reference
24. User interface Bus
25. Fosc input
26. Square signal
27. Sine wave OSC
28. Activation time TON
29. Deactivation time TOFF
30. Modulated signal Mod-out
31. Gain factor Gain
32. Output_enable signal

A preferred embodiment of the present invention may consist of an ultrasounds treatment system that comprises a centralized web services platform (WSP), a software application (APP), a portable ultrasounds treatment equipment (UTE), a set of programmable electronic prescriptions (PEP), and at least one digital electronic treatment file (ET).

The WSP consists of a load balancer (1) which distributes service requests among one or more servers (2) internally communicated with a single database (3) through a local area network (4) not accessible from outside. Through an identity verification system, authorized users may use the permanent services that the WSP offers from the Internet: a) authorize third parties to make use of the APP to perform maintenance on UTEs and PEPs; b) discharge patients, establish their diagnosis and prescribe electronic treatments (ETs) to their patients; c) set the technical characteristics of the ETs associated with each diagnosis; d) review the data collected in the UTE during treatment sessions; e) evaluate the effectiveness of the prescribed treatments; f) share ETs and their assessments with other professionals; g) establish dialogues and consultations with other professional users of the WSP.

The ET is a digital file that includes data about patient identity, diagnosis, all the technical parameters of the prescribed treatment, and a digital signature that ensures that the previously described data have not been manipulated by unauthorized parties The PEP is a physical device with enough capacity to store at least an ET, as an example: NFC cards, USB storage devices, memory cards and printed QR codes, among others.

The APP is a software application available for different platforms that allows to perform a number of functions: a) schedule a PEP with the ET prescribed to a patient; b) completely erase a PEP and/or data stored in an UTE; c) activate a UTE with an ET prescribed to a patient; d) dump the data recorded in the UTEs during the various sessions of treatment on the WSP; and e) update the software of the UTE.

The UTE comprises the following modules: a power supply (5), a battery (6), a system controller (7), a non-volatile memory (8), a communication card (9), a real-time clock (10), a user interface (11), a RF oscillator (15), a pulse modulator (16), a transducer amplifier (17), an internal o external piezoelectric transducer (18), and a monitor of therapy (19). The communication card (9) is the module responsible of both reading the PEP as well as establishing a bidirectional communication with any device that runs the APP through compatible communication. As the subsystem responsible of the digital data transfer with external devices may communicate accordingly with one or more protocols and standards such as NFC (ISO 14443), WiFi (IEEE 802.11), Ethernet (IEEE 802.3), Bluetooth (IEEE 802.15) or USB.

In a different embodiment of the present invention, for the specific treatment of costal and sternal fractures, their consolidation delays and postsurgical thoracic pain, the ETU emits a non-modifiable dose of pulsed ultrasound of 1 Mhz frequency, 0.5 W/cm$^2$, 50 mw/cm$^2$ and 1 min/cm$^2$ of duration.

The method to carry out treatment according to the present invention starts form a program that can set the following functioning modes in the UTE: standby mode (READY), treatment mode (RUN), treatment-in-pause mode (PAUSE), data dump mode (DUMP) and program update mode (FLASH). At least READY, RUN and DUMP modes must be present, with FLASH and PAUSE modes being optional.

In READY mode, the UTE is in low-power mode, with the RF oscillator (15), pulse modulator (16), transducer amplifier (17), piezoelectric transducer (18) and monitor therapy (19) disconnected from the power supply and therefore temporarily disconnected. The UTE displays a summary of the device status to the patient through the user interface (11), specifically: the date and time, level of battery charge (6), and whether the battery is charging or not. When the communication card (9) receives incoming data (either from a PEP or from any device running the APP with a compatible communications protocol), the system controller (7) verifies the authenticity and integrity of the data. If the ET is valid, the current date and time and the time elapsed from the last treatment are within the range established in the ET, the UTE will go to RUN mode. If the received message is a memory dump command, the UTE will go to DUMP mode and if it is a program update request, the UTE will go to FLASH mode.

In RUN mode, the UTE displays through the user interface (11) the remaining time of treatment and instructions for positioning and fixing to the body the piezoelectric transducer (18). In this mode, the UTE delivers the treatment assigned and calculates and stores in its nonvolatile memory (8) the power transmitted to the patient in mW/cm$^2$ and compares this value to that stored in the ET, acting on the gain factor Gain (31) of the amplifier transducer (17) so that the potency transmitted to the patient matches the nominal potency of the treatment. Once the programmed treatment time has concluded, the ETU returns to READY mode. The patient has the option to pause the treatment momentarily at any time during the treatment. If this happens, or when an alarm is triggered, the UTE goes to PAUSE mode. Alarm conditions include: detection that the UTE is plugged to the mains, battery level too low, or detection of short circuits or open circuits in the piezoelectric transducer (18). Both the ultrasounds potency delivered to the patient and the alarms triggered during the treatment are stored in the nonvolatile memory (8) of the UTE.

In PAUSE mode, the remaining time of treatment is stopped, and the output potency that goes into the transducer amplifier (17) is deactivated. If the patient requests to continue with the treatment through the user interface (11) and there are not alarm conditions, the UTE will return to RUN mode.

In DUMP mode, all information recorded in the nonvolatile memory (8) is sent through the communication card (9). Once the data transfer has been successfully confirmed, the system controller (7) deletes data stored in the nonvolatile memory (8) and the UTE goes to RUN mode.

In FLASH mode, the UTE receives a sequence of bytes though the communication card (9) and checks that the transmission has been correct. If so, the system controller (7) deletes the program memory of the microcontroller and writes on it the new received sequence of bytes. Next, the system controller (7) goes to RUN mode and the microcontroller initiates with the new program.

The present invention can be applied to different uses, among which are the following:

Use of the system and method for the ultrasound treatment of bone fractures in general and their consolidation delays Ultrasound treatment of limb fractures and their consolidation delays Ultrasound treatment of osteo-muscular and tendon injuries Ultrasound treatment of acute or chronic postsurgical pain Ultrasound treatment of osteonecrosis Ultrasound treatment of thoracic, costal, sternal factors and their consolidation delays Ultrasound treatment of costal and sternal factors and their consolidation delays and of postsurgical thoracic pain with a portable generator that emits a non-modifiable dose of pulsed ultrasound of 1 Mhz frequency, 0.5 W/cm$^2$ intensity, applied to 10% using 1 ms pulses every 9 ms (50 mw/cm$^2$) with a duration of 1 min/cm$^2$ of area to be treated.

The invention claimed is:

1. A system for ultrasounds treatment of bone fractures, osteo-muscular-tendon injuries, postsurgical pain and osteonecrosis in a field of medicine and veterinary comprising:

a centralized web services platform (WSP), a software application (APP), a portable ultrasounds treatment equipment (UTE), a set of programmable electronic prescriptions (PEP), and at least one electronic treatment file (ET), with the WSP comprising a load balancer that distribute services requests among one or more servers, characterized by being internally communicated with a single database through a local area network not accessible from outside; and wherein:

the ETU comprises the following modules: a power supply, a battery, a system controller, a non-volatile memory, a communication card, a real-time clock, a user interface, a RF oscillator, a pulse modulator, a transducer amplifier, an internal or external piezoelectric transducer, and a monitor of therapy; and developing stages wherein:

in first stage, in READY mode, the UTE is in a low-power mode, and the RF oscillator, pulse modulator, transducer amplifier, piezoelectric transducer and monitor therapy are disconnected from the power supply and therefore temporarily disconnected, so that when the communication card receives incoming data either from a PEP or from any device running the APP with a compatible communications protocol, the system controller verifies an authenticity and integrity of the data and if the ET is valid, a current date and time and a time elapsed from a last treatment are within the range established in the ET, the UTE will go to RUN mode whereas if the received data is a memory dump command, it will go to DUMP mode and if it is a program update request, it will go to FLASH mode;

in a second stage, in RUN mode, in which the UTE delivers an assigned treatment and calculates and stores periodically in its nonvolatile memory a power transmitted to tho patient in mW/cm$^2$ compares this value to that stored in the ET, acting on the gain factor Gain of the amplifier transducer so that a potency transmitted to the patient matches a nominal potency of the treatment, and once a programmed treatment time has concluded, the ETU returns to READY mode, (taking into account that the patient has the option to pause the treatment momentarily at any time during the treatment and that, if this happens, or when an alarm is triggered), the UTE will go to PAUSE mode; alarm conditions include: detection that the UTE is plugged to the battery and the battery level too low, or detection of short circuits or open circuits in the piezoelectric transducer, both the ultrasounds potency delivered to the patient and the alarms triggered during the treatment being stored in the nonvolatile memory of the UTE;

in PAUSE mode, in which the treatment is stopped, and the output potency that goes out of the transducer amplifier is deactivated; if the patient requests to continue and there are not alarm conditions, the UTE will return to RUN mode;

in a third stage, in DUMP mode, all information recorded in the nonvolatile memory is sent through the communication card and once the data transfer has been successfully confirmed, the system controller deletes data stored in the nonvolatile memory and the UTE goes to RUN mode;

in a fourth stage, in FLASH mode, the UTE receives a sequence of bytes though the communication card and checks that the transmission has been correct, if so, the system controller deletes a program memory of the microcontroller and writes on it the new received sequence of bytes; next, the system controller goes to RUN mode and the microcontroller initiates with a new program.

2. A system for ultrasounds treatment of bone fractures, osteo- muscular-tendon injuries, postsurgical pain and osteonecrosis in the field of medicine and veterinary of claim 1, the ET being a digital file that includes data about the patient identity, diagnosis, all the technical parameters of a prescribed treatment, and characterized by having a digital signature that ensures that those data have not been manipulated by unauthorized parties.

3. A system for ultrasounds treatment of bone fractures, osteo-muscular-tendon injuries, postsurgical pain and osteonecrosis in the field of medicine and veterinary of claim 1, in which the previously mentioned PEP is a physical device with enough capacity to store at least one as, for example: NFC cards, USB storage devices, memory cards, characterized by storing those devices printed QR codes.

4. A system for ultrasounds treatment of bone fractures, osteo-muscular-tendon injuries, postsurgical pain and osteonecrosis in the field of medicine and veterinary of claim 1, in which the previously mentioned APP is a software application available for different platforms characterized by performing a number of functions: (a) schedule the PEP with the ET prescribed to the patient; (b) completely erase the PEP and/or data stored in the UTE; (c) activate the UTE with the ET prescribed to the patient; (d) dump the data recorded in the UTEs during the various sessions of treatment on the WSP; and (e) update the software of the UTE.

5. A method of treatment, with the system of claim 1, of costal and sternal factors and their consolidation delays and of postsurgical thoracic pain with a portable generator that emits a non-modifiable dose of pulsed ultrasound of 1 Mhz frequency, 0.5 W/cm$^2$ intensity, applied to 10% using 1 ms pulses every 9 ms (50 mw/cm$^2$) with a duration of 1 min/cm$^2$ of area to be treated.

* * * * *